United States Patent [19]
Spitzer et al.

[11] 4,422,877
[45] Dec. 27, 1983

[54] SYNTHETIC POLYMER-PROPELLANT COMPOSITIONS FORMING COLD FOAMED STRUCTURES HAVING A TEMPERATURE AT LEAST 30° C. BELOW AMBIENT TEMPERATURE AND CONTAINING OPEN AND/OR CLOSED CELLS

[75] Inventors: J. George Spitzer, Palm Beach, Fla.; Lloyd I. Osipow, New York, N.Y.

[73] Assignee: Restech Research Limited Partnership, New York, N.Y.

[21] Appl. No.: 345,833

[22] Filed: Feb. 4, 1982

Related U.S. Application Data

[63] Continuation-in-part of Ser. No. 200,847, Oct. 28, 1980, abandoned, and Ser. No. 308,054, Oct. 2, 1981, abandoned.

[51] Int. Cl.³ .............................................. C08J 9/14
[52] U.S. Cl. ................................. 106/122; 106/180; 106/188; 106/190; 106/191; 521/78; 521/79; 521/114; 521/111; 521/131; 521/132; 524/903
[58] Field of Search ............... 521/78, 98, 79, 111, 521/114, 131, 132; 106/122, 180, 188, 190, 191

[56] References Cited

U.S. PATENT DOCUMENTS

| | | | |
|---|---|---|---|
| 3,572,330 | 3/1971 | Gander | 521/78 |
| 3,705,669 | 12/1972 | Cox et al. | 521/78 |
| 3,912,665 | 10/1975 | Spitzer et al. | 521/78 |
| 3,912,666 | 10/1975 | Spitzer et al. | 521/78 |
| 3,912,667 | 10/1975 | Spitzer | 521/78 |

Primary Examiner—Morton Foelak

[57] ABSTRACT

Synthetic polymer-propellant compositions are provided that are capable of forming foamed structures having a temperature at least 30° C. below ambient temperature and containing open and/or closed cells, which may optionally contain a material which is deposited in the pores and/or walls of the structure as the structure is formed, and comprising:

(a) a film-forming synthetic polymer is an amount within the range from about 2% to about 30% by weight of the composition;

(b) at least one liquefied propellant boiling below −10° C;

(c) the total propellant being in an amount within the range from about 50% to about 90% by weight of the composition; and having a heat of vaporization of at least 55 calories per gram; the propellant being capable of dissolving the synthetic polymer at least in the presence of a co-solvent that is soluble in the propellant and in solutions of the synthetic polymer in the propellant at ambient temperature; and (d) at least one nonsolvent that is soluble in the propellant solution but in which the synthetic polymer is insoluble in an amount within the range from about 1% to about 85% by weight of the composition; the composition forming upon volatilization of propellant at ambient temperature and pressure a foamed structure containing open and/or closed cells and having a temperature at least 30° C. below ambient temperature.

18 Claims, No Drawings

SYNTHETIC POLYMER-PROPELLANT COMPOSITIONS FORMING COLD FOAMED STRUCTURES HAVING A TEMPERATURE AT LEAST 30° C. BELOW AMBIENT TEMPERATURE AND CONTAINING OPEN AND/OR CLOSED CELLS

This application is a continuation-in-part of Ser. No. 200,847, filed Oct. 28, 1980, and of Ser. No. 308,054, filed Oct. 2, 1981, both now abandoned.

A propellant is defined by the Chemical Specialties Manufacturers' Association as a liquefied gas with a vapor pressure greater than atmospheric pressure at a temperature of 105° F. A large class of organic compounds falls in this category, of which some are hydrocarbons, but most are halogenated hydrocarbons having one or two carbon atoms, and one or more chlorine, fluorine or bromine atoms. Frequently, different halogens are substituted in the same molecule to impart the desired vapor pressure.

Because of their high volatility propellants have been used as pore-forming agents in the production of plastic foams for many years. Propellants are soluble in many synthetic resins, and accordingly can be absorbed in the solid resin, which is desirably in particulate form, after which the resin containing the absorbed propellant is subjected to heat and pressure. The propellant vaporizes, and a closed cell foam structure is formed. U.S. Pat. No. 3,335,101 shows application of this process to the production of foams of chlorinated polyethylene. U.S. Pat. Nos. 2,387,730, 2,948,665, and 3,351,569 foam polyethylene and polypropylene in this way; U.S. Pat. No. 3,160,688 foams polystyrene; U.S. Pat. No. 3,352,802 foams polyvinyl chloride; U.S. Pat. No. 3,253,967 foams polyoxymethylene, and U.S. Pat. No. 3,305,497 foams polyurethanes. U.S. Pat. No. 3,310,617 foams a variety of thermoplastic resins by a similar but modified process intended to ensure that the propellant is uniformly dissolved or dispersed in the molten resin, so as to overcome the poor mixing problems of prior procedures.

In these procedures the amounts of propellants used are rather small, because only small amounts of the propellant can be absorbed in the solid resin, and the resin is molten, to facilitate foaming of the structure when the propellant is volatilized in situ to form the cells. The resin is then allowed to solidify before the structure can collapse, so as to preserve the foamed nature.

Randa, U.S. Pat. No. 3,072,583, patented Jan. 8, 1963, prepares foamed articles by extruding a perfluorocarbon resin in molten form, and containing from 0.1% to 5% by weight of a fluoromethane. The fluoromethane dissolves in the resin at atmospheric pressure and room temperature, and is volatilized under the extrusion conditions so as to produce a foamed structure. This procedure is useful for coating wire with a foamed coating.

Raley and Skochdopole, U.S. Pat. No. 3,379,802, patented Apr. 23, 1968, describe a similar procedure for aliphatic olefin polymer blends, and U.S. Pat. No. 3,067,147 makes cellular polyethylene using 1,2-dichloro-1,1,2,2-tetrafluoroethane.

It has also been proposed that ultramicrocellular fibers be prepared with the aid of propellants. Blades and White, U.S. Pat. Nos. 3,227,664 and 3,227,784, patented Jan. 4, 1966, describe a flash extrusion process for this purpose. Supple, ultramicrocellular shaped structures are obtained from synthetic organic crystalline polymers by heating a confined mixture of the polymer plus at least one activating liquid at a temperature and pressure at which a homogeneous solution is formed, the temperature being greater than the normal boiling point of the liquid. This solution is then extruded abruptly to a region of substantially lower pressure and temperature under such conditions that a very large number of bubble nuclei exist at the extrusion orifice. Vaporization of the activating liquid rapidly cools the solution to the temperature at which the polymer precipitates and freezes in the polymer orientation produced in the rapid extrusion and expansion process.

The activating liquids must meet a number of requirements, of which one of the most noteworthy is that the liquid should dissolve less than 1% of the polymeric material at or below its boiling point. In other words, it is a nonsolvent for the polymer at or below its boiling point, but a solvent for the polymer under the extrusion conditions. To provide bubble nuclei at the instant of extrusion, a particulate solid nucleating agent can be incorporated in the polymer solution. Silica aerogel is a suitable nucleating agent. The result is a structure having extremely small closed cells. Modifications of this process are described in U.S. Pat. No. 3,081,519 to Blades et al, dated Mar. 19, 1963, U.S. Pat. Nos. 3,375,211 and 3,384,531 to Parrish, dated Mar. 26, 1968 and May 21, 1968, U.S. Pat. No. 3,375,212 to Bonner, issued Mar. 26, 1968, U.S. Pat. No. 3,461,193 to Gilardi, dated Aug. 12, 1969, and U.S. Pat. No. 3,467,744 to Woodell, dated Sept. 16, 1969.

Certain synthetic resins are soluble in propellants at room temperature. Bunting, U.S. Pat. No. 2,716,637, patented Aug. 30, 1955, pointed out that when such solutions are volatilized quickly, fine bubbles of plastic resin are obtained, which initially retain sufficient solvent so as to possess a surface tackiness, but as the solvent continues to escape from the globules. they blister and acquire an unsatisfactory appearance. Bunting avoids this by combining a fatty acid with the resin propellant solution, and keeps the resin content of the solution rather low, within the range from 5 to about 12%. Similar compositions are described by Hochberg and Pellerano, U.S. Pat. No. 2,773,855, patented Dec. 11, 1956, and these workers point out that the particles obtained are in the form of small, hollow or solid semispheres ranging from 1/16 or ¼ inch in largest dimension. Coherent foamed masses are not obtained.

Gander, U.S. Pat. No. 3,419,506, patented Dec. 31, 1968, prepares a protective film covering or dressing for wounds by dispensing from a pressurized container a composition comprising a film-forming vinyl acetate polymer or alkyl acrylate polymer, from 10 to 50% by weight based on the solids of a finely-divided filler, and a propellant, the solution having a viscosity of at least 1000 cp at normal room temperature. The inert filler must be present in order to obtain satisfactory foamed application of the film-forming resin, according to Gander, the filler perhaps serving as a nucleating agent, as described by Blades et al in U.S. Pat. Nos. 3,227,784 and 3,227,664, and rather thin, tacky films are obtained, several mils in thickness.

Spitzer et al U.S. Pat. No. 3,912,667, patented Oct. 14, 1975, provides synthetic polymer-propellant compositions which comprise a film-forming synthetic polymer in an amount within the range from about 10 to about 60% by weight of the composition in solution in a liquid propellant boiling below 45° F. at atmospheric pressure and retained in the composition in the liquid phase at a superatmospheric pressure, the propellant being in a sufficient amount within the range from about 20 to about 70% by weight of the composition to form upon rapid volatilization of the propellant at atmospheric temperature and pressure a coherent, voluminous foamed structure containing open and/or closed cells; and dispersed or dissolved in the composition an additive in an amount within the range from about 5 to about 700% by weight of the polymer, in excess of the amount soluble in the polymer in the absence of the propellant, and which is deposited in the cells of the structure when the propellant volatilizes, and which can be removed from the cells of the structure, any organic liquid present which is a solvent for the polymer and boils at or above 45° F. at atmospheric pressure being in an amount from about zero up to about three times and preferably up to about twice the amount of polymer present in the composition.

The additive that may subsequently be disposed in the cells and/or walls of the foamed structure can be in solution in the propellant, or dispersed in the propellant, or in solution or in dispersion as a separate liquid phase that is itself dispersed in the propellant phase of the composition. The additive may also be the sole component of a separate liquid phase that is itself dispersed in the propellant phase of the composition. Thus, the propellant compositions of the invention can be solutions or emulsions in which the propellant is the solvent in the continuous phase and another liquid or liquid composition or solid which is the additive is dispersed therein in a discontinuous phase. Since the propellant boils at a temperature below 7° C., it is of course a vapor at room temperature and pressure. Consequently, the propellant compositions of the invention are stored in closed containers capable of withstanding the pressure of the propellant, so as to maintain the propellant in the liquid phase. When the composition is ejected from the container to atmospheric pressure at atmospheric (room) temperature, the propellant is rapidly volatilized, and a coherent foamed structure is formed, with the additive in the cells and/or walls.

Spitzer et al U.S. Pat. No. 3,912, 666, patented Oct. 14, 1975, provides emulsified synthetic polymer propellant compositions of the oil-in-water type in which water is the continuous phase, and the solution of synthetic polymer in a propellant is the discontinuous phase. The essential components of these oil-in-water emulsions are an aqueous solution comprising a foam-stabilizing agent, which is the aqueous phase, and an oil phase consisting essentially of a polymer dissolved in liquefied propellant which is also a foaming agent. Thus, when the pressurized composition packaged in a container is expelled through a valve into the atmosphere, the liquefied propellant immediately volatilizes, and foams both the oil phase and the aqueous phase, causing them to expand and the polymer to precipitate, resulting in a foamed structure.

Spitzer et al U.S. Pat. No. 3,912,665, patented Oct. 14, 1975, provides synthetic polymer-propellant compositions in which an organic liquid that also may comprise a foaming agent or foam-stabilizing agent serves as the continuous or dispersing phase for a solution consisting essentially of a polymer dissolved in liquefied propellant, which is a foaming agent. The organic liquid is present in an amount greater than its solubility in the polymer propellant phase. In the case of water-soluble organic liquids, a minor amount of water may be added to reduce its solubility in the polymer propellant phase, and thus ensure the presence of an organic liquid phase. The organic liquid is a liquid at atmospheric temperature and pressure, whereas the propellant is a gas under these conditions. Thus, when the pressurized composition packaged in a container is expelled through a valve into the atmosphere, the liquefied propellant immediately volatilizes, and foams the propellant phase, causing it to expand and the polymer to precipitate, resulting in the foamed structure, with the organic liquid phase in the foam cells thereof.

As indicated in the disclosures of these patents, such foamed structures are cool to the touch when prepared because of the cooling effect of volatilization of the propellant, but not so cold as if the liquefied propellant were present alone, because of the heat-diluting effect of the other ingredients, including the synthetic polymer, which is often present in major amount in the foamed structure.

From the heat of vaporization of the propellant, the percent by weight of propellant in the composition, and the weight of product expelled from the container, one can readily calculate a theoretical capacity for the pad to absorb heat, i.e., the cooling capacity of the pad. However, this is a maximum value. Part of the propellant evaporates as the composition is being expelled from the container, and there is no way to predict to what extent heat of vaporization of this portion of the propellant is drawn from the pad, cooling it, and to what extent from the environment. Further, propellant gas that leaves the pad at a lower temperature than ambient temperature does not draw heat from the pad, and thus part of the cooling capacity is wasted. In addition to these effects, the initial temperature of the pad and the length of time the pad remains cold will depend on the boiling point of the propellant, the weight of pad expelled, the density of the pad, its thickness, and its insulating qualities.

The result is that it is quite difficult to so adjust these variables as to form a foamed structure that is sufficiently cold, and will remain cold for a long enough time to make it useful as a cold pad or ice pack.

Ice packs, for example, can be cooled to a temperature well below 0° C. in a freezer. However, they quickly absorb heat, and part of the ice begins to melt. During the entire period that the pack contains both ice and water, the temperature within the pack is at 0° C. The heat of fusion of ice and the quantity of ice present determine the capacity of the pack to absorb heat, which can be for a long period of time. When a surface temperature probe is pressed against an ice pack containing some liquid water, a temperature reading of about 5° C. is obtained. This is about 15° C. below normal ambient indoor temperature. The 5° C. measurement is contrasted with the 0° C. value obtained by immersing the temperature probe in a mixture of ice and water.

Similarly, temperature measurements were made with the pads, with the probe on a tissue placed on top of the pad. If the pad is wrapped around the probe, lower temperature readings are obtained.

It is quite difficult so to formulate a synthetic polymer-propellant composition that a cold foamed structure is produced whose temperature initially is well below 0° C., and that will maintain this temperature for a period of time. The temperature of the structure will not be maintained for as extended a period as an ice pack in any case, because the size of the pad is limited, and once the propellant is volatilized, there is of course no more cooling effect. Since volatilization of the propellant is necessary in order to foam the structure in the first place, it is not normally possible to retain appreciable amounts of propellant in the foamed structure, to maintain the cold temperature for a considerable period of time after the structure has been formed.

In accordance with the present invention, it has been determined that the coldness effect, i.e., the temperature of the foamed structure produced from a pressurized synthetic polymer liquefied propellant composition, can be reduced to at least 30° C. below the ambient temperature at which the foamed structure is formed, if the composition comprises as the essential ingredients:

(a) a film-forming synthetic polymer in an amount within the range from about 2% to about 30% by weight of the composition;

(b) at least one liquefied propellant boiling below −10° C.;

(c) the total propellant being in an amount within the range from about 50% to about 90% by weight of the composition; and having a heat of vaporization of at least 55 calories per gram; the propellant being capable of dissolving the synthetic polymer at least in the presence of a co-solvent that is soluble in the propellant and in solutions of the synthetic polymer in the propellant at ambient temperature; and (d) at least one nonsolvent that is soluble in the propellant solution but in which the synthetic polymer is insoluble in an amount within the range from about 1% to about 85% by weight of the composition; the composition forming upon volatilization of propellant at ambient temperature and pressure a foamed structure containing open and/or closed cells and having a temperature at least 30° C. below ambient temperature.

In one form of the invention, sufficient nonsolvent liquid is present to form at least two liquid phases, each phase containing synthetic polymer and propellant. In this form, the relative proportions of the above three essential ingredients and whether a co-solvent is needed, and if so, how much, is determined by trial-and-error experimentation. The following technique is suggested as one approach:

The synthetic polymer is dissolved in the propellant to prepare a synthetic polymer-propellant solution. A co-solvent is added, if necessary to dissolve the polymer in the propellant. Nonsolvent liquid is then added, with mixing until the solution displays the first detectable opacity which does not disappear after additional shaking.

The first detectable opacity signifies phase separation and the existence of at least two separate phases, and the proportions of propellant, any co-solvent, and nonsolvent required for two-phase formation. A series of solutions are then prepared, using slightly more and slightly less nonsolvent, and the samples are stored and observed for several days. When insufficient nonsolvent is present to cause phase separation, the composition will remain transparent and essentially colorless. When just sufficient nonsolvent has been added to cause phase separation, the composition will generally show Tyndall colors: it will appear orange when the sample is between the eye and the light source, and blue when the eye is at right angles to a line drawn from the light source to the center of the sample. Upon increase in the proportion of nonsolvent to solvent, turbidity will increase and Tyndall colors may disappear. Further increase in the proportion of nonsolvent results in opacity, rapid separation of the phases into layers, and increasing viscosity of the phase most concentrated in polymer.

It is preferred that there be sufficient nonsolvent present to form at least two liquid phases, as evidenced by the presence of Tyndall colors, or turbidity, or opacity, but insufficient nonsolvent to increase the viscosity of any phase that separates to above about 1000 centipoises at 21° C.

If two different synthetic polymers are used with differing solubilities in the propellant, it may be possible to form a two or poly liquid phase synthetic polymer-propellant composition without the addition of a nonsolvent. In this case, the several liquid phases may be composed of propellant and any co-solvent, if required, with a major proportion of one polymer in one phase, and a major proportion of the second polymer in the second phase, and with minor proportions of each polymer in the other phase.

One of the phases of the synthetic polymer-propellant solution will contain a higher concentration of polymer and a lower concentration of nonsolvent than the other phase.

The two synthetic polymer-propellant phases may be mutually emulsifiable to form a stable or unstable emulsion. If unstable, and the viscosity of the phases is below about 1000 centipoises at 21° C., the two phases or layers are readily emulsified together, and they can be expelled together through the open valve of a conventional aerosol container, even if the emulsion is unstable.

However, the preferred composition is a stable emulsion of the two liquid synthetic polymer-propellant phases. This may be a colloidal or an opaque emulsion, and preferably has a viscosity below 1000 centipoises at 21° C., to facilitate complete expulsion from the container.

A small amount of a third liquid phase which is of a gel-like viscosity may also form when the synthetic polymer is composed of polymer molecules with a broad range of molecular weights. If the higher molecular weight fraction be not soluble in the solvent-nonsolvent combination used to form the two liquid phases containing the bulk of the synthetic polymer, it may precipitate out as a gel-like material. This material is not expelled with the remainder of the composition, however, and is not deleterious.

Additional liquid phases as well as dispersed solids may also be present in the composition.

It is rather surprising that it is possible to form foamed structures that are at least 30° C. below ambient temperature. Normal indoor temperature is about 21° C., and 30 degrees less is about −9° C. Thus, the temperature of the foamed structure will approximate the boiling temperature of the propellant. At that temperature, a substantial proportion of the propellant will be retained, and further evaporation will occur slowly.

In contrast, the foamed structures of the prior art became cool, but not cold. This permitted rapid evaporation of propellant, and the foamed structure formed as a consequence of this rapid loss of propellant.

It is theorized that the reason a foamed structure does form, even though a substantial amount of propellant is temporarily retained, is that once the composition is expelled from the container there is a further separation of the major polymer-propellant phase into two liquid phases, one of which is highly concentrated in polymer and has a low concentration of propellant, and the other is mostly propellant with very little polymer. It is the phase that is highly concentrated in polymer that forms the walls of the foamed structure.

As the propellant, there is used in the compositions of the invention at least one volatile propellant that has a boiling temperature below −10° C. at atmospheric pressure. One or a mixture of propellants can be used, but the boiling temperature of the mixture need not be below −10° C.

The propellant or mixture of propellants has a heat of vaporization of at least 55 calories per gram, and is chemically inert to the synthetic resin and the additive that may be present in the compositions.

At least one nonsolvent that is soluble in the propellant solution but in which the synthetic polymer is insoluble is required, in an amount within the range from about 1% to about 85% by weight of the composition.

In one preferred form of the invention, sufficient nonsolvent should be present to form at least two liquid phases, as evidenced by the presence of Tyndall colors, or turbidity, or opacity, but preferably insufficient nonsolvent to increase the viscosity of any phase that separates to above about 1000 centipoises at 21° C.

In another preferred form, the presence of a second liquid phase is not required. Instead, it is preferred that there be present at least one polar propellant that is water-soluble in an amount of at least 0.2% by weight at 21° C., and that has a higher vapor pressure than any nonpolar propellant present. The polar propellant can also meet the boiling temperature and heat of vaporization requirements, in which event only one propellant may be needed, but this is not essential.

When such polar propellant is present, any one or more of the following components should be included in the composition, to promote separation of the polymer-propellant phase into two liquefied propellant phases:

(a) a non-polar liquefied propellant, defined as one that is soluble in water to at most 0.05% by weight at 21° C. and atmospheric pressure, that is a nonsolvent for the polymer, and that has a lower vapor pressure than the polar liquefied propellant, (b) a liquid or solid nonsolvent that is appreciably soluble in the propellant, and in which the propellant is appreciably soluble, but that is not compatible with the polymer, and separates from the remainder of the composition as propellant evaporates. Examples of nonsolvents include mineral, vegetable, and silicone oils;

(c) water or aqueous solution.

In the special case of synthetic cellulose polymers, it has been found that a polar propellant is a preferred but not an essential component of the composition. However, if a polar propellant is not included in the composition, it is necessary to include both the nonsolvent component (b) above, and the water or aqueous solution, component (c) above.

A polar propellant may often be a solvent for the polymer, while the nonpolar propellant is a nonsolvent, and promotes phase separation. By preparing and testing blends of the two types of propellants in a suitable composition, a satisfactory proportion can be determined.

The polar propellant has the higher vapor pressure of the two propellants, and during propellant evaporation in forming the foamed product the polar propellant is lost. Since this is the solvent propellant, the result is preferentially a tendency for phase separation. If the ratio of polar to nonpolar propellant in the composition is too high, the blend will remain in one phase during evaporation, liquid phase separation will not occur, and a foamed structure will not form for some time. On the other hand, if the ratio of polar to nonpolar solvent is too low, phase separation may occur so rapidly and to so pronounced an extent that the foamed structure shreds as it forms, or there is a excessively rapid bleeding of propellant-containing liquid from the structure.

If neither the polar nor the nonpolar liquid is a solvent for the polymer, a suitable blend of the two types of propellants may nonetheless be a solvent for the polymer. Sometimes a co-solvent is required to bring the polymer into solution. In the preferred case, the ratio of the two propellants is adjusted to give a composition with one liquid propellant phase in the container, or with just a slight excess of the nonpolar propellant. If there is an excess of the more volatile polar propellant, this may result in formation of two liquid propellant phases inside the container. When such a product is dispensed, propellant evaporation will result in a blend that has improved solvent action for the polymer, and a foamed structure will not form for some time.

Nonsolvent materials such as mineral oils that have good solubility in the propellants, are good solvents for the propellants, and are not compatible with the polymer, can often be used in compositions containing low concentrations of polymer to promote the formation of a foamed structure. Preferably, the composition has only one liquid propellant phase in the container. When product is dispensed, and propellant simultaneously evaporates, mineral oil or equivalent containing an appreciable proportion of propellant bleeds from the foamed structure as it is forming. It is the removal of propellant in liquid form in addition to propellant evaporation that enables a foamed structure to form.

Water or an aqueous solution can often be used to advantage in compositions that contain a blend of polar and nonpolar propellants to promote phase separation and the formation of a foamed structure. The reason for this can only be conjectured. It should first be noted that evaporation is a cooling process, and some degree of cooling occurs whenever product is dispensed. An effect of cooling in generel is to reduce the solubility of the polymer in the solvent. This can be significant. However, it can be particularly important when water is present. Since the polar propellant is more soluble in water than the nonpolar solvent, and the solubility of liquefied propellants in water increases substantially with a reduction in temperature, in the case of the more water-soluble polar propellants the preferential loss of the more volatile polar propellant by evaporation coupled with the preferential extraction of this propellant by water at a cold temperature causes the propellant blend to quickly become a poor solvent for the polymer, and this results in separation of the polymer-propellant solution into two liquid propellant phases.

Nonpolar propellants that can be used include propane, n-butane, isobutane, cyclopropane, 1-butene and 2-butene.

Useful polar propellants include halogenated hydrocarbons such as chlorodifluoromethane (Propellant 22), 1-chloro-1, 1-difluoroethane (Propellant 142B), 1, 1-difluoroethane (Propellant 152A), and dimethyl ether.

Properties of various representative propellants are summarized in Table I. Any combinations of these propellants that meet the various requirements called for above may be used.

TABLE I

| | Heat of Vaporization at boiling point (Calories/gram) | Boiling Point (°C.) | Vapor Pressure at 21° C. (p.s.i.g) | Solubility in Water (Weight %) |
|---|---|---|---|---|
| Polar Propellants | | | | |
| Chlorodifluoromethane (Propellant 22) | 55.9 | −41 | 122.5 | 0.3% at 25° C. |
| Dichlorofluoromethane (Propellant 21) | 77.9 | 8.9 | 8.4 | 0.7% at 30° C. |
| 1,1-difluoro-1-chloroethane (Propellant 142B) | 53.3 | −9.2 | 30 | 0.2% at 21° C. |
| 1,1-difluoroethane (Propellant 152A) | 78 | −24.7 | 63 | 0.3% at 21° C. |
| Dimethyl ether | 111.6 | −24.8 | 60 | 7% at 18° C. |
| Ethyl Chloride | 91.3 | 12.4 | 5.3 | 0.6% at 21° C. |
| Nonpolar Propellants | | | | |
| n-butane | 87.5 | −0.5 | 16.3 | |
| 1-butene | 93.4 | −6.3 | 13.1 | |
| 2-butene (cis) | 99.5 | 3.7 | 13.2 | |
| 2-butene (trans) | 96.9 | 0.9 | 15.1 | |
| cyclopropane | 113.9 | −33 | 75 | |
| isobutane | 87.6 | −11.7 | 30.7 | |
| propane | 101.8 | −42 | 109.6 | |
| Propellants with Heat of Vaporization below 45 cals/g | | | | |
| Bromotrifluoromethane (Propellant 13B1) | 28 | −58 | 190 | |
| Dichlorodifluoromethane (Propellant 12) | 39.4 | −30 | 70.2 | |
| 1,2-dichlorotetrafluoroethane (Propellant 114) | 32.8 | 3.6 | 12.9 | |
| Octafluorocyclobutane (Propellant C318) | 27.7 | −6 | 25 | |
| Trichlorofluoromethane (Propellant 11) | 43.5 | 23.8 | 13.4 (p.s.i.a.) | |

Propellants with a low heat of vaporization can be used in blends with propellants having a high heat of vaporization to obtain a composition with a calculated heat of varporization for the mixture of at least 55 calories per gram.

If both a polar propellant and a nonpolar propellant are present, the polar propellant has the higher vapor pressure and the lower boiling point. In view of the requirement that at least one propellant have a boiling point below about −10° C., the only polar propellants that can be used in substantial amounts are Propellants 22, 142B, 152A and dimethyl ether.

The nonpolar propellants n-butane and the butenes can be used with any of the above four polar propellants, with the expectation that the solubility of the polymer in the propellant phase decreases during discharge, due to preferential evaporation of the polar propellant. Similarly, isobutane can be used with Propellants 22, 152A and dimethyl ether, but not with Propellant 142B.

The first essential ingredient of the compositions of the invention is the synthetic polymer. Any thermoplastic polymer can be used, as disclosed in U.S. Pat. Nos. 3,912,667, 3,912,666 and 3,912,665, that can be rendered in powdered or granular form, and that can be dissolved in a liquefied propellant, alone or with the aid of one or more co-solvents or materials that show solvent properties in the combination.

Thermoplastic polymers as a class, thermosetting polymers in a propellant-soluble stage of polymerization, and propellant-soluble polymers capable of being cross-linked can be used. The polymerization or cross-linking of the latter two types of polymers can be effected during or after the structure has been formed, to set the structure. Alkyl acrylate and alkyl methacrylate polymers and copolymers, such as ethyl methacrylate,-butyl methacrylate, isobutyl methacrylate, 50/50 n-butyl/isobutyl methacrylate copolymers, 25/75 lauryl-/isobutyl methacrylate copolymer, 30/70 stearyl/t-butyl methacrylate copolymer, 50/50 ethyl/n-butyl methacrylate copolymer, copolymers of acrylic and vinyl compounds, such as 50/50 vinyl toluene/isobutyl methacrylate copolymer, 50/35/15 vinyl toluene/t-butyl methacrylate/stearyl methacrylate terpolymer, 50/50 ethyl acrylate/vinyl acetate copolymer, certain other vinyl polymers, such as polyvinyl acetate, vinyl toluene-butadiene copolymers, carboxylated vinyl acetate, certain cellulose derivatives, such as ethyl cellulose, cellulose acetate, cellulose propionate, cellulose acetate butyrate and cellulose acetate propionate, and certain silicone polymers such as Silicone XC-20997, are soluble in propellants of the class set forth.

Polymers which can be set to a solvent-insoluble stage of polymerization chemically or by radiation include urethane prepolymers, unsaturated polyesters such as unsaturated alkyd polymers, and polyolefins such as polybutylene and poly-2-methylbutene-1.

The polymer should have a molecular weight within the range from about 10,000 to about 1,000,000. Polymers of molecular weights below about 10,000 may not have sufficient cohesive strength to form a cohesive foamed structure, while those with molecular weights in excess of about 1,000,000 may be insoluble in propellant solvents. Polymers having molecular weights within the range from about 25,000 to about 600,000 are preferred.

The relative proportions of the second essential ingredient, the propellant, and the polymer in the synthetic polymer-propellant compositions of the invention determine to a considerable extent the nature of the foamed structure that is formed, when the pressure upon the composition is reduced to atmospheric and the propellant allowed to volatilize. If the proportion of polymer is too low (and usually the lower proportion is not less than approximately 2% polymer by weight of the composition) a cohesive foamed structure is not formed, but instead a bubbly, sticky, flowable mass is obtained. If the material is expelled as a spray, through a fine orifice, a plurality of foamed particles are obtained, similar in some respects to the decorative particles obtained according to U.S. Pat. Nos. 2,716,637 and 2,773,855 referred to above. If the proportion of propellant is too low, i.e., if the polymer concentration exceeds about 30%, the foamed structure will not be sufficiently cold to be of practical value.

In addition to the propellant and the synthetic polymer, and especially if the propellant is a poor solvent for the polymer, the compositions can include additional less volatile or relatively nonvolatile co-solvents, which may be solvents for the polymer, or alternatively solvents for any additive that may be present, or which may be solvents for both the polymer and the additive.

A nonsolvent is the third essential ingredient of the compositions of the invention. The nonsolvent is preferably a liquefied propellant, but any organic liquid or solid can be used that is incompatible with the synthetic polymer, i.e. insoluble in the polymer, and in which the polymer is insoluble. The nonsolvents for the polymers are known, and any propellant listed above or co-solvent listed below that is a nonsolvent for the particular synthetic polymer selected can be used. Liquid mineral oils, vegetable oils, and silicone oils are exemplary.

There may also be present plasticizers for the polymer, coloring agents, fillers for the polymer which modify the polymer, if the polymer is in a partially polymerized condition, so that polymerization can be completed after the foamed structure has been formed, to set the structure in a desired configuration.

It is usually preferred that liquid components of the propellant composition boiling at or above $-10°$ C. that are not propellants, but are soluble in the propellants, and that act as co-solvents or as nonsolvents for the polymer not exceed about three times and preferably not exceed about twice the weight of the polymer present, and in most cases they should not exceed the weight of the polymer present. In general, the amount of such co-solvent or nonsolvent should also not be greater than the amount by weight of propellant present. However, the exact amount that can be tolerated will depend upon the partitioning of the polymer among the several liquid polymer-propellant solution phases. No phase that separates should contain so much polymer that its viscosity exceeds about 1000 cps at $21°$ C. Thus, the selected amount has to take into account the concentration of polymer in the propellant composition, as well as whether the liquid is a good or poor solvent for the polymer. Emulsifying agents can also be added in order to obtain reasonably stable emulsions.

Liquids which are higher boiling than the propellant will modify the foamed structure. If they are also solvents for the polymer they may also plasticize the polymer during the period after the propellant has been volatilized, and before the remaining less volatile solvent is fully volatilized. Such a transitional plasticized stage can be useful in forming the foamed structure into a desired configuration, and it may also aid in the formation of a higher proportion of closed or nonruptured cells.

Examples of co-solvents and nonsolvents that boil above $-10°$ C. include dichlorofluoromethane, trichlorofluoromethane, 1,1,2-trichloro-1,2,2-trifluoroethane, 1,2-dibromo-1,1,2,2-tetrafluoroethane, 1,1,2,2-tetrachloro-1,2-difluoroethane, methanol, ethanol, acetone, methyl isobutyl ketone, benzene, toluene, xylene, chloroform, methylchloroform, methylene chloride, 1,1,1-trichloroethane, and perchloroethylene.

Plasticizers can also be incorporated; these are selected according to the nature of the polymer, and since they are nonvolatile permanently soften the foamed structure.

Plasticizers which may be useful include butyl phthalyl butyl glycolate, tributyl citrate, acetyltributyl, citrate, tricresyl phosphate, dibutyl tartrate, dibutyl phthalate, di-2-ethylhexyl azelate, chlorinated biphenyl and methyl abietate.

Fillers for the polymer can be used as extenders for the polymer, and may also modify the physical properties of the foamed structure. The filler usually has a small particle size, although fibrous material also can be used. Satisfactory fillers include chalk, talc, silica, diatomaceous earth, clay, asbestos, magnesium silicate, calcium silicate, magnesium stearate, kaopolite, powdered polyethylene and powdered polystyrene. The filler can be from 0 to 300% by weight of the resin. Coloring agents including dyes and pigments are used in small proportions, ranging from 0 to 10% by weight of the resin.

Any additive that is not attacked by the propellant or polymer can be incorporated in the propellant compositions of the invention, and is present in an amount in excess of that which is dissolved in the polymer (if any) after the propellant has been volatilized, and the additive will remain in the foamed polymer structure after the propellant has been volatilized. The additive will always be found in the cells after the structure is formed. If a liquid is present in the cells too, and the additive is soluble in the liquid, an additive solution is present in the cells. If, in addition, the additive is compatible with or soluble in the polymer, it will be found in the polymer matrix as well, and this is particularly so when the additive is a solid and no liquid is present. The liquid if present will also permeate the polymer if it is soluble therein, and any additive solution therein will do the same, if this be so. Incompatibility of the additive with the polymer can be ensured by providing a liquid solvent for the additive that is itself incompatible with the polymer, thus ensuring that the additive is dissolved in the solvent, and the resulting solution is found in the cells of the structure.

Apart from these requirements, which are purely physical, any type of additive can be employed, depending upon the intended use for the cold foamed structure.

The cold foamed structures of this invention for example, can be applied externally in the treatment of physical injuries and for the relief of pain, such as to a sprained joint to reduce swelling. Applied to a burn, they will reverse the thermal shock, and help prevent blistering. Cold can help stop bleeding and slow the spreading of venom from an insect or snake bite. These effects can be realized without addition of an additive, but in some instances it is advantageous to include an additive such as an antiseptic or analgesic.

The foamed structures of the invention are useful as cold applicator pads for cold external or topical application of cosmetics of all types, such as those intended for cleansing, conditioning, lubricating, and protecting the skin, hormone preparations, suntan preparations, skin lighteners and bleach creams, foundation makeups, eye makeups, pre-shave and after-shave preparations, depilatories, hair grooming preparations, permanent wave preparations, hair straightening preparations, anti-dandruff preparations, bath preparations, nail lacquers and removers, antiperspirants and deodorants, fragrance-imparting preparations, perfumes, baby toiletries, and hypoallergenic cosmetics. They are also useful cold applicators for soap and synthetic detergent preparations of all types for personal washing, laundering, dishwashing, cleansing of silver, shampoos, shaving soaps and creams, hair coloring and dye removers, wave sets, lacquers, rinses and conditioners, and dry shampoos. They are also useful for cold application of medicaments of all types, antimicrobal agents, such as bactericides and antifungal agents of all types, and antibiotics, for external application, such as topical or rectal, for instance, as suppositories.

Exemplary medicaments that can be combined in the propellant compositions of the invention include the antihistamines; sulfa drugs, for example, sulfadiazine, sulfabenzamide, sulfacetamide, sulfanilamide, sulfapyridine, sulfathiazole, sulfapyrazine, sulfaguanidine, sulfaphthalidine, sulfasuxidine, sulfaoxazole, sulfamylon, phthalylsulfacetamide, N'-3,4-dimethylbenzoylsulfanilamide, benzylsulfanilamide and N'-2-(2-quinoxalyl) sulfanilamide; lipotropic agents, such as methionine, choline, inositol and beta-sitosterol and mixtures thereof; local anesthetics, such as benzocaine and pramoxine hydrochloride; essential oils, such as menthol, eucalyptus oil and eugenol; salts of penicillin, such as potassium penicillin G, procaine, penicillin G, 1-ephenamine penicillin G, dibenzylamine penicillin G, and other penicillin salts disclosed in U.S. Pat. No. 2,627,491; phenoxymethyl penicillin and salts thereof; additional antibiotic agents, such as streptomycin, dihydrostreptomycin, bacitracin, polymixin, tyrothricin, erythromycin, chlortetracycline, oxytetracycline, tetracycline, oleandomycin, chloramphenicol, magnamycin, novobiocin, cyclosterine and neomycin; vitamins, for instance, Vitamins A, $A_1$, $B_1$, $B_2$, $B_6$, $B_{12}$, and members of the family, folic acid and members of that family, and vitamins C, $D_2$, $D_3$ and E; hormones, such as cortisone, hydrocortisone, 9-α-fluorocortisone, 9-α-fluorohydrocortisone, prednisone and prednisolone; anabolic agents, such as 11,17-dihydroxy-9-α-fluoro-17-o-methyl-4-androsten-3-one and 17-α-ethyl-19-nortestosterone; and additional antimicrobial agents, such as mycostatin, mercurichrome, iodine, methiolate, hexachlorophene, tribromosalicylanilide, trichlorocarbanilide, and undecylenic acid.

These medicaments can be compounded in the forms of solutions and elixirs with suitable solvents and dispersants, such as are conventionally used in such formulations. Aqueous and alcoholic solutions usually are used. The amount of medicament is not critical and is chosen to meet the need; usually, from 0.02 to about 15% is adequate.

Cleansing compositions can be formulated containing single or multiple detergents, such as soaps and anionic synthetic detergents or soaps and nonionic synthetic detergents, or they can be composed wholly of synthetic detergents, including the anionic, cationic and nonionic types. As used herein the term "detergent" includes soaps and synthetic detergents, including the anionic, cationic aand nonionic types.

Typical satisfactory anionic nonsoaps are the alkyl sulfates, such as sodium lauryl sulfate; the alkyl aryl sulfonates, such as sodium polypropylene benzene or toluene sulfonates and the sodium keryl benzene or toluene sulfonates; the sulfated ethoxynated phenols, such as the ammonium salt of sulfated ethoxynated nonyl phenol, prepared by condensation of nonyl phenol with five moles of ethylene oxide; the sodium fatty acid esters of taurine, such as sodium palmitic or oleic methyl tauride or mixtures thereof; the esters of higher fatty acids and hydroxy ethane sulfonates, such as oleic acid ester of hydroxy ethane sodium sulfonate; sodium lauroyl sarcosinate; sodium stearoyl lactate; sodium lauroyl lactate; sodium dioctyl sulfosuccinte; sodium lauroyl isethionate, and sodium lauryl sulfoacetate. Also useful are nonionic nonsoaps, such as the polyethylene glycol esters of the higher fatty acids, for example, polyethanoxy esters of lauric, myristic, palmitic and stearic acids, polyethanoxy ethers of lauryl alcohol, cetyl alcohol, oleyl alcohol and lanolin alcohol, the polyethanoxy ethers of alkyl phenols, such as the condensation product of octyl and nonyl phenol with five to fifty moles of ethylene oxide; the higher fatty acid esters of sorbitanethylene oxide condensates, such as the polyethanoxy esters of sorbitan monostearate; polyethanoxypolypropanoxy polyols. Cetyltrimethylammonium bromide is a typical cationic nonsoap.

The term "soap" as used herein refers to alkali metal, ammonium, and amine soaps of the saturated and unsaturated higher fatty acids having from about eight to about twenty-six carbon atoms, such as capric, caprylic, lauric, myristic, palmitic, stearic, oleic, linoleic, linolenic, arachidic, behenic, margaric, tridechoic, and cerotic acids and the mixtures of such acids naturally occurring in fats, oils, waxes and rosins, such as the soaps of coconut oil fatty acids, tallow fatty acids, lard fatty acids, fish oil fatty acids, beeswax, palm oil fatty acids, sesame oil fatty acids, peanut oil fatty acids, olive oil fatty acids, palm kernel oil fatty acids, corn oil fatty acids, babassu oil fatty acids, rosin acids, abietic acid, and greases.

Cleaning and abrasive compositions can also contain as additives water-soluble alkaline salts, including sodium silicate, borax, sodium carbonate and trisodium phosphate. Sequestering agents that are soluble in water, such as sodium hexametaphosphate, pentasodium tripolyphosphate, tetrasodium pyrophosphate, and the sodium salts of ethylenediaminetetraacetic acid or nitrilotriacetic acid, can also be used as additives, alone or with cleaning and scouring compositions.

When soaps or synthetic detergents are included in the polymer-propellant composition for the purpose of cleaning, other ingredients may also be present, such as sequestering agents, abrasives, foam boosters, and conditioning agents. These components may be present in the propellant composition in the form of a dispersed powder or dispersed liqiud. The cleaning components may also be dissolved in a liquid that is emulsified in the polymer-propellant solution. However, the type and quantity of liquid used must be selected with care. For example, soaps and synthetic detergents that are effective water-soluble cleansing agents are also hydrophilic emulsifying agents and exhibit a pronounced tendency to form emulsions in which water is the continuous phase. To avoid this situation, which can result in the failure to form an applicator pad, the proportion of water present in the liquid phase containing the soap or synthetic detergent should be quite low, or the phase volume should be small as compared with the volume of the polymer-propellant solution. Often, it is advantageous to employ the cleaning components in the form of a powder dispersed in the polymer-propellant solution. After forming the foam structure, the cleaning agents are made available by soaking the applicator pad in water.

Germicidal detergent compositions can also be formulated, including, for instance, the 2,2'-dihydroxyhalogenated diphenyl methanes, such as G-11.

In one form of this invention, a co-dispensing valve may be used. Such valves are capable of simultaneously mixing and dispensing materials from two separate compartments. Thus, one compartment would contain the pad-forming composition and the other would contain the cosmetic or other additive. In this instance, somewhat more leeway is possible regarding the formulation of the additive preparation. However, if the latter contains too hydrophilic an emulsifier system, an applicator pad is not likely to form. Similarly, components of the additive that are likely to dissolve the polymer foam structure rapidly should be avoided.

The pressurized polymer liquefied propellant compositions of the invention are converted into foamed polymer structures when the pressure is released to atmospheric and the propellant is permitted to volatilize. This is easily accomplished after pressure reduction, with an initially rapid volatilization of part of the propellant followed by a period of up to one half hour or more of much slower volatilization of propellant after the structure has become cold, by storing the liquefied propellant composition in a closed container wherein the autogenous pressure is sufficient to maintain the propellant in the liquid phase. Then, when the structure is desired, a volume of the composition is dispensed and the pressure thereby rapidly reduced to atmospheric pressure at room temperature, whereupon the propellant volatilizes and the cold foamed structure is formed. The propellant composition may also be stored in a closed container, under applied pressure greater than the autogenous pressure arising from the propellant itself to facilitate expelling the composition from the container, as through a valve or orifice, into the atmosphere. Because of the high volatility of the propellants employed, the polymer structure is nonsticky, unless a plasticizer or other nonpropellant solvent for the polymer is also present in sufficient amount to impart a sticky characteristic to the polymer. If the structure is to be adhered to a surface, stickiness can be desirable. In the case of a solvent that also volatilizes, although more slowly than the propellant, this sticky condition is transitory, however, and exists only until the solvent has been removed. Excessive stickiness is undesirable in a cold applicator pad.

If a composition formulated to produce a pad with a high proportion of closed cells is ejected into a confined space, such as a mold, preferably closed, the foamed structure will acquire the configuration of the mold, and a molded object is obtained. The molding can be carried out at room temperature, without application of external pressure, since a pressure sufficient to ensure that the structure conforms to the configuration of the mold is obtained upon volatilization of a portion of the propellant at atmospheric pressure and temperature.

If the composition is ejected into the atmosphere, the foamed structure will have an irregular shape. It is quite convenient, in practicing this embodiment of the invention, simply to eject the composition from the container into the hand, forming a pad of any desired size, which is controlled by controlling the duration of the ejection period. For this purpose, the polymer liquefied propellant compositions of the invention are suitably packaged in aerosol containers of the standard type, the valve being controlled by one hand, and the foamed structure being received in the other. The foamed structure is formed almost instantaneously, and the applicator pad is ready for use within seconds after the procedure has begun. The structure is shape-retaining because of the nature of the polymer used, and it is also flexible initially because of the retention of some propellant, even if no plasticizer is present, i.e., if the polymer is a rigid polymer.

Alternatively, the valve actuator may be shaped as a dish or a hemisphere so that it acts as a receptacle or mold for the foamed structure as it is being formed, and the interior shape of the receptacle or mold determines the shape of the foamed structure.

The compositions can be stretched to some extent and compacted as the foamed structure is being formed, and in this way can be made to conform to the shape of the object upon which it is being applied, so as to form a covering or a coating. When applied to the body, for example, a coating including a medicament for release to the skin can be formed, which can be allowed to remain in contact with the skin for long periods, for slow release of the medicament over a long period of time. However, because the compositions are converted into a foamed structure within a few seconds, they are not actually flowable, and will not spread voluntarily. In this respect, they differ from conventional aerosol paints or lacquers, from which the solvent is removed only slowly, and which are consequently flowable, and can be spread out to a film that may be only a few mils thick, and they also differ from the spreadable compositions described in U.S. Pat. No. 3,419,506 to Gander.

Prior to expulsion from the container, however, the compositions are flowable. At a viscosity below 1000 cps at 21° C., the fluid composition is sufficiently flowable to be ejected from the container under pressure. The viscosity corresponds to a quickly flowable liquid.

In the event that the propellant employed in the compositions of the invention has a sufficient vapor pressure at ambient temperature, it will also serve as a propellant to expel the material from the pressurized container in which it is confined. In the event that its vapor pressure is insufficient, additional pressure may be provided in the container by a suitable pressurizing gas, such as nitrogen, nitrous oxide or carbon dioxide. Because commercial regulations limit the total pressure of common aerosol containers to not more than about 150 psig, the propellant employed is preferably one whose vapor pressure in the propellant does not exceed this limit.

The following Examples represent preferred embodiments of the invention in the opinion of the inventors:

EXAMPLES 1 TO 7

In these Examples polyisobutyl methacrylate is used to illustrate one preferred form of the invention, requiring at least two liquid phases containing polymer and propellant. Polyisobutyl methacrylate is a good film former, the foam structure expands readily and the foam density tends to be low. Isobutane used as the major propellant is not a solvent for the polymer. Ethanol and corn oil are co-solvents, corn oil having in addition a weak plasticizing action, and ethanol having a fugitive plasticizing action and lowering the viscosity of the polymer solution.

The compositions were prepared by weighing the ingredients into a pressurized aerosol container, storing the container in an oven at 45° C. overnight, and then shaking with a mechanical shaker until the polymer had dissolved. The foam density was determined by expelling the aerosol composition into a 6 cc clear plastic cup, and determining the weight of foamed composition collected.

The temperature of the foam was determined using a tele-thermometer fitted with a surface probe, 4.5±0.5 g of foam was collected on a sheet of paper tissue, and temperature was sensed with the probe pressed against the tissue.

The lowest temperature obtained was reported as the initial temperature. Temperature was monitored until the temperature had increased to +5° C. and the time from collection to +5° C. is reported as "cold time".

The weight of product collected was determined by weighing the container before and after expelling the product. Table II gives the results, compared with Controls A, B and C which do not have a sufficient proportion of nonsolvent to form at least two liquid phases, each containing synthetic polymer and propellant.

TABLE II

|  | Control A | Example 1 | Example 2 | Control B | Example 3 | Example 4 | Example 5 | Example 6 | Control C | Example 7 |
|---|---|---|---|---|---|---|---|---|---|---|
| | | | | | Parts By Weight | | | | | |
| Polyisobutyl methacrylate[1] | 31.8 | 28.6 | 20.5 | 24.8 | 22.0 | 22.0 | 19.8 | 21.6 | 15.2 | 15.7 |
| Corn oil | 8.0 | 10.7 | 10.3 | 12.4 | 11.0 | 8.2 | 9.9 | 8.1 | 11.0 | 7.9 |
| Ethanol | 3.4 | | 5.1 | 2.7 | 1.6 | | | | 1.1 | 1.1 |
| Mineral oil | | | 1.5 | | | | | | | |
| Miranol C2M-SF[2] | | | 0.2 | | | | | | | |
| Water | | | 1.3 | | | | | | | |
| Isobutane | 56.8 | 53.6 | 48.9 | 60.1 | 65.4 | 59.3 | 61.0 | 60.0 | 65.8 | 53.8 |
| Propane | | | 12.2 | | | | | | | |
| Dimethyl ether | | 7.1 | | | | 10.4 | 9.4 | 10.3 | 6.9 | 21.5 |
| % Propellant | 56.8 | 60.7 | 61.1 | 60.1 | 65.4 | 69.7 | 70.4 | 70.3 | 72.7 | 75.3 |
| Foam density g/cc | 0.58 | 0.66 | 0.45 | 0.20 | 0.45 | 0.37 | 0.55 | 0.55 | 0.33 | 0.35 |
| Initial temperature °C. | −5 | −10 | −9 | −5 | −11 | −13 | −18 | −14 | −8 | −15 |
| Time to reach +5° C., minutes | 7 | 12 | 9 | 9 | 12 | 12 | 16 | 12 | 8 | 12 |

[1]Molecular weight about 200,000
[2]Amphoteric disodium dicarboxylic coconut oil fatty acids imidazoline derivative

EXAMPLES 8 AND 9

The preferred form of the invention requiring liquid phase separation is again illustrated, as in Examples 1 through 7. In these Examples, ethyl hydroxyethyl cellulose is used, a relatively poor film former; the foam structures expand little, if at all, and the foam density tends to be high. Isobutane used as the major propellant is not a solvent for this cellulose derivative. Ethanol and corn oil are co-solvents, corn oil having in addition a weak plasticizing action, and ethanol having fugitive plasticizing action and lowering the viscosity of the EHEC solution.

The compositions were prepared by weighing the ingredients into a pressurized aerosol container, storing the container in an oven at 45° C. overnight, and then shaking with a mechanical shaker until the polymer had dissolved. The foam density was determined by expelling the aerosol composition into a 6 cc clear plastic cup, and determining the weight of foamed composition collected.

The temperature of the foam was determined using a telethermometer fitted with a surface probe. 4.5±0.5 g of foam was collected on a sheet of paper tissue, and temperature was sensed with the probe pressed against the tissue.

The lowest temperature obtained was reported as the initial temperature. Temperature was monitored until the temperature had increased to +5° C. and the time from collection to +5° C. is reported as "cold time". The weight of product collected was determined by weighing the container before and after expelling the product. Table III gives the results, in comparison with Controls D and E, which do not have a sufficient proportion of nonsolvent to form at least two liquid phases, each containing synthetic polymer and propellant.

TABLE III

|  | Control D | Example 8 | Control E | Example 9 |
|---|---|---|---|---|
| | Parts By Weight | | | |
| EHEC, extra low viscosity[1] | 21.4 | 18.6 | 18.3 | 19.8 |
| Corn oil | 2.9 | 2.5 | 1.5 | 2.6 |
| Ethanol | 4.3 | 3.7 | 2.3 | 4.0 |
| Miranol C2M-SF[2] | | 1.3 | | 0.7 |

TABLE III-continued

|  | Control D | Example 8 | Control E | Example 9 |
|---|---|---|---|---|
| | Parts By Weight | | | |
| Water | | 11.7 | | 6.7 |
| Isobutane | 53.5 | 46.6 | 57.2 | 49.6 |
| Dimethyl ether | 17.9 | 15.6 | 19.1 | 16.6 |
| % Propellant | 71.4 | 62.2 | 76.3 | 66.2 |
| Foam density, g/cc | 0.47 | 0.9 | 0.53 | 0.83 |
| Initial temperature, °C. | −11 | −14 | −12 | −14 |
| Time to +5° C., minutes | 7 | 12 | 9 | 18 |

[1]Ethyl hydroxyethyl cellulose (Hercules, Inc. extra low viscosity grade, 10–20 cps).
[2]Amphoteric disodium dicarboxylic coconut oil fatty acids imidazoline derivative.

Examples 10 through 20 illustrate a preferred form of the invention in which a polar propellant is used and any one or more of the following components are included in the composition to promote separation of the polymer-propellant phase into two liquefied propellant phases:

(a) a nonpolar liquefied propellant with a lower vapor pressure than the polar liquefied propellant;
(b) a liquid or solid nonsolvent for the polymer;
(c) water or aqueous solutions.

Example 21 illustrates the special case of synthetic cellulose polymers, where a polar propellant is preferred but not essential. If a polar propellant is not present, then it is necessary to include both the nonsolvent component (b) above, and the water or aqueous solution, component (c) above.

EXAMPLE 10

Three pressurized polymer-liquefied propellant compositions were prepared to the following formulations:

|  | Example 10 | Control F | Control G |
|---|---|---|---|
| | Parts By Weight | | |
| Ethyl methacrylate polymer | 6.3 | 8.9 | 7.8 |
| Acetyl tributyl citrate (Citroflex A-4) | 1.6 | 2.2 | 2.0 |
| Mineral Oil, 65–75 SSU (Drakeol 7) | 28.6 | — | 11.8 |
| Dimethyl ether | 63.5 | 88.9 | 78.4 |

The ethyl methacrylate polymer, Citroflex A-4 and Drakeol 7 were placed in metal aerosol containers. The valves were clinched into position, and the liquefied dimethyl ether was introduced under pressure. The cans were shaken on a paint shaker until the polymer had completely dissolved. A portion of the contents of each container was then transferred to a glass pressure bottle for observation. All three compositions were clear, low viscosity solutions, with one liquid phase.

The three pressure bottles were stored in a refrigerator at 4° C. for three hours and examined. Example 10 had separated into two liquid phases, of which the lower was more viscous, and occupied about 30% of the volume. Controls F and G remained in a single liquid phase.

It will be noted that Example 10 contained the most mineral oil, a nonsolvent for the polymer. Control F contained none, and Control G less than half that of Example 10. After shaking, product was dispensed from each of the three aerosol cans at room temperature through foam actuators. Controls F and G dispensed bubbly, sticky liquids, from which propellant volatilized quickly, but which remained liquid thereafter and did not form a foamed structure. Example 10 dispensed a mass of nonflowable material that quickly swelled into a tough foamed structure suitable for use as an applicator pad. It was cold, and it exuded mineral oil.

It is apparent from these results that the mineral oil acts to promote the separation of the polymer-propellant solution into two liquid phases containing propellant. Example 10 shows that the mineral oil must be present in a sufficient amount, in order for a foamed structure to form fairly quickly.

A 5.3 gram sample of the Example 10 compositions was dispensed onto a paper towel, and the temperature of the foamed structure was determined using an electronic thermometer fitted with a 1 cm diameter surface probe. The minimum temperature of the structure was −22° C., as compared with a boiling point of −25° C. for dimethyl ether. It required 8 minutes for the foamed structure to warm to 0° C. The ambient temperature was 25° C.

A sample of the Example 10 composition was expelled into a tared weighing dish and found to weigh 4.7 grams. The sample was reweighed after 60 seconds, by which time a foamed structure had already formed, and found to still contain 40% propellant. The composition of Example 10 contained 36.5% nonpropellant (polymer, acetyl tributylcitrate and mineral oil). The 4.7 g sample thus contained 4.7×0.365=1.72 g nonpropellant. The sample in the weighing dish after 60 seconds weighted 2.84 g. Then, 100×1.72/2.84=60% nonpropellant, and 100−60=40% propellant.

EXAMPLE 11

|  | Parts By Weight | |
|---|---|---|
|  | Example 11 | Control H |
| Isobutyl methacrylate polymer (Elvacite 2045) | 5.4 | 6.5 |
| Corn Oil | 2.0 | 2.5 |
| Triethyl citrate (Citroflex 2) | 0.8 | 1.0 |
| Imidazoline dicarboxylic coconut derivative, sodium salt 10% concentrate in water (Miranol C2M-SF) | 16.5 | — |
| Isobutane | 45.5 | 54.5 |
| 1,1-difluoroethane | 29.8 | 35.5 |

The Elvacite 2045, Citroflex 2 and corn oil were placed in an aerosol can, the valve was clinched in place, and the liquefied propellants were added through the valve. The cans were then shaken on a paint shaker until the polymer had completely dissolved. In Example 11, the aqueous Miranol solution was added through the valve.

Example 11 and Control H have the same composition, except for the presence of the aqueous solution in Example 11.

Portions of the compositions in each can were dispensed using foam actuators. Example 11 quickly formed a tough foamed structure, suitable for use as an applicator. It felt cold and damp. Control H deposited a sticky, bubbly liquid, which remained liquid after volatilization of propellant and did not form a foamed structure. Example 11, thus showed that the aqueous Miranol solution was essential to foam pad on structure formation.

A sample of the composition of Example 11 was dispensed onto a paper towel, and the temperature of the foamed structure was measured as in Example 10. The foam had a minimum temperature of −24° C., and required 11 minutes to warm to 0° C., with the ambient temperature at 26° C.

Using the procedure described in Example 10, it was found that the foamed structure from 3.9 g of expelled Example 11 product contained 35% propellant after 60 seconds.

EXAMPLE 12

|  | Parts By Weight | | |
|---|---|---|---|
|  | Example 12 | Control 8 | Control J |
| Isobutyl methacrylate polymer (Elvacite 2045) | 7.2 | 7.2 | 7.2 |
| Mineral Oil, 65–75 SSU (Drakeol 7) | 7.2 | 7.2 | 7.2 |
| Isobutane | 55.2 | 52.5 | 58.0 |
| 1,1-difluoroethane | 30.4 | 33.1 | 27.6 |

All ingredients except the liquefied propellants were placed in aerosol cans. The valves were clinched on and the liquefied propellants were added through the valves. The cans were shaken on a paint shaker until the polymer had dissolved.

Samples of the compositions were dispensed using foam actuators. Example 12 rapidly formed a soft, oily foamed structure that felt very cold. Control I was expelled as a bubbly, sticky liquid which remained liquid after volatilization of the propellants, and did not form a foamed structure while Control J expelled as an oily propellant liquid which upon volatilization of propellant formed an oily foamed structure, with a considerable volume of oily liquid left over.

Example 12 and the two controls differ only in the ratio of isobutane to 1,1-difluoroethane, with Example 12 corresponding to the optimum ratio for this system, as determined by trial and error.

Control I contains too high a ratio of 1,1-difluoroethane to isobutane. Even after preferential loss of 1,1- difluoroethane by evaporation during dispensing, the solvent action for the polymer is still very good, and a foamed structure does not form.

Control J contains too low a ratio of 1,1-difluoroethane to isobutane, so that there are two liquid layers in the container. Even though the sample is shaken immediately before dispensing, the product is dispensed as a mixture of the two liquid phases, and is unsatisfactory.

A 6.5 gram portion of Example 12 was dispensed onto a paper towel, and the temperature of the foamed structure was determined using an electronic thermometer with a 1 cm diameter surface probe. The sample had a minimum temperature of −33° C., and required 6 minutes to warm to 0° C., with the ambient temperature at 25° C.

Using the procedure described in Example 10, it was found that the foamed structure from 6.0 g of expelled Example 12 composition contained 70% propellant after 60 seconds.

EXAMPLE 13

|  | Parts By Weight | |
|---|---|---|
|  | Example 13 | Control K |
| Ethyl Cellulose, T-50 | 7.2 | 9.6 |
| Mineral Oil, 65-75 SSU (Drakeol 7) | 3.6 | — |
| Octyl Dodecanol (Standamul G) | 1.8 | — |
| Imidazoline monocarboxylic stearyl derivative, sodium salt 10% concentrate in water (Miranol DM-SF) | 19.2 | — |
| Isobutane | 20.1 | 26.6 |
| Dimethyl ether | 48.1 | 63.8 |

All ingredients except the propellants were placed in aerosol cans. The valves were clinched on and the liquefied propellants were added through the valves. The cans were shaken on a paint shaker until the polymer had dissolved.

Product was dispensed through a foam actuator. Control K upon expulsion yielded an ointment, while Example 13 yielded a foamed structure that was tough enough to be rubbed on the skin without tearing. The two compositions contained the same ratio of isobutane to dimethyl ether.

Portions of both compositions were transferred to glass pressure bottles. Control K was a single liquid layer, slightly turbid and fluid. Example 13 was also of low viscosity and appeared as a single liquid layer, but it was more turbid than Control K.

A 7.6 sample of Example 13 was expelled and the temperature of the foamed structure was measured, as in Example 10. It had a minimum temperature of −20° C., and required 18 minutes to warm to 0° C., with the ambient temperature at 26° C.

Using the procedure described in Example 10, it was found that the foamed structure from 4.3 of expelled product contained 39% propellant after 60 seconds.

EXAMPLE 14

|  | Parts By Weight | |
|---|---|---|
|  | Example 14 | Control L |
| Ethyl hydroxyethyl cellulose high viscosity | 7.0 | 7.3 |
| Mineral Oil, 65-75 SSU (Drakeol 7) | 13.1 | 13.7 |
| Propylene glycol stearate (Emerest 2381, Self-emulsifying) | 3.5 | 3.6 |
| Imidazoline monocarboxylic stearyl derivative, sodium salt 10% concentrate in water (Miranol DM-SF) | 4.4 | — |
| Isobutane | 48.6 | 50.9 |
| Dimethyl ether | 23.4 | 24.5 |

All the ingredients except the propellants were placed in aerosol cans. The valves were clinched on, and the liquefied propellants were added through the valves. The cans were then shaken on a paint shaker until the polymer had dissolved.

The samples were dispensed through a foam actuator. Control L formed a thick but flowable ointment. Example 14 formed a solid foamed structure that was tough enough to be rubbed on the skin without tearing.

Portions of the samples were transferred to glass pressure bottles. Both appeared as single liquid layers. Control L was turbid, while Example 14 was almost clear, exhibiting a very slight haze, and pronounced Tyndall colors.

The samples were then stored overnight in a refrigerator at 4° C. Control L appeared essentially unchanged. Example 14 had two liquid layers; the upper liquid laayer was clear, slightly viscous and occupied about 15% of the liquid volume. The lower layer was more viscous and turbid, but clarified and showed Tyndall colors when it warmed to room temperature.

When mixed at room temperature and allowed to remain undisturbed, it did not show any evidence of layering, even after several months.

A 4.5 g portion of Example 14 was dispensed onto a paper towel and the temperature was measured as in the previous Examples. A minimum temperature of −17° C. was obtained. Eight minutes was required for the foam to warm to 0° C., with the ambient temperature at 25° C.

Using the procedure described in Example 10, it was found that the foamed structure from 8.5 g of expelled product contained 42% propellant after 60 seconds.

EXAMPLE 15

|  | Parts By Weight | |
|---|---|---|
|  | Example 15 | Control M |
| Ethyl hydroxyethyl cellulose, high viscosity | 6.0 | 7.8 |
| Glyceryl ester of hydrogenated rosin (Staybelite Ester 10) | 6.0 | 7.8 |
| Tributyl citrate (Citroflex 4) | 3.8 | 4.7 |
| Imidazoline monocarboxylic stearyl derivative, sodium salt 10% concentrate in water (Miranol DM-SF) | 22.5 | — |
| Isobutane | 41.7 | 53.8 |
| Dimethyl ether | 20.0 | 25.9 |

All the ingredients except the propellants were placed in aerosol cans. The valves were clinched in place, and the liquefied propellants were added through the valves. The samples were then shaken on a paint shaker until the polymer had completely dissolved.

The samples were then dispensed through foam actuators, Control M formed a fluid ointment. Example 15 formed a solid foamed structure, which was tough enough to be used for rubbing after a few seconds.

Portions of the samples were transferred to glass pressure bottles. Control M showed some haze. Example 15 was more turbid. After several months at room temperature it separated into a lower aqueous layer and two liquid propellant layers. Control M did not change during this period.

A 9 g portion of Example 15 was dispensed onto a paper towel, and the temperature was measured as in the previous Examples. A minimum temperature of $-14°$ C. was obtained. It required 10 minutes for the foamed structure to warm to 0° C. with the ambient temperature at 25° C.

Using the procedure described in Example 10, it was found that the foamed structure from 8.8 g of expelled product contained 39% propellant after 60 seconds.

EXAMPLES 16 and 17

|  | Parts By Weight | | |
| --- | --- | --- | --- |
|  | Example 16 | Example 17 | Control N |
| Ethyl hydroxyethyl cellulose, high viscosity | 7.2 | 7.8 | 7.8 |
| Propylene glycol monostearate | 3.9 | 4.4 | 4.3 |
| Tributyl citrate (Citroflex 4) | 1.6 | 1.7 | 1.7 |
| Mineral Oil, 65–75 SSU (Drakeol 7) | 9.5 | 10.5 | — |
| Imidazoline monocarboxylic stearyl derivative, sodium salt 10% concentrate in water (Miranol DM-SF) | 5.2 | — | — |
| Ethanol | 0.7 | — | — |
| Isobutane | 52.6 | 58.2 | 62.7 |
| 1,1-difluoroethane | 21.3 | 17.4 | 23.4 |

All the ingredients except the propellants were placed in aerosol cans. The valves were clinched in place, and the liquefied propellants were added through the valves. The samples were then shaken on a paint shaker until the polymer had completely dissolved.

The samples were dispensed through foam actuators. Control N formed a sticky paste. Example 17 formed a foamed structure suitable for use as a dressing, but it was too weak for rubbing. Example 16 formed a tough foamed structure, suitable for rubbing on the skin.

Portions of the samples were transferred to glass pressure bottles and examined. Control N had two liquid propellant layers. Example 17 had one slightly turbid liquid layer and exhibited Tyndall colors. Example 16 was similar in appearance to Example 17, but after several days at room temperature it separated into two liquid propellant layers of equal volume, while Example 17 did not separate, even after one month.

Portions of the samples were dispensed onto paper towels and the temperature determined as in the previous Examples.

A foam from a sample 4.1 g of Example 16 had a minimum temperature of $-17°$ C. It required 12 minutes for the foamed structure to warm to 0° C., with the ambient temperature at 25° C.

Similarly, the foamed structure from 7 g of Example 17 had a minimum temperature of $-21°$ C., and required 13 minutes to warm to 0° C.

Using the procedure described in Example 10, it was found that the foamed structure from 4.4 g of expelled Example 16 composition contained 53% propellant after 60 seconds. The foamed structure from 5.7 g of expelled Example 17 composition contained 49% propellant after 60 seconds.

EXAMPLE 18

|  | Parts By Weight | |
| --- | --- | --- |
|  | Example 18 | Control O |
| Isobutyl methacrylate polymer (Elvacite 2045) | 7.6 | 7.6 |
| Triethyl citrate (Citroflex 2) | 1.2 | 1.2 |
| Isobutane | 61.8 | 58.8 |
| 1,1-difluoroethane | 29.4 | 32.4 |

All the ingredients except the propellants were placed in aerosol cans. The valves were clinched in place and the liquefied propellants were added through the valves. The samples were then shaken on a paint shaker until the polymer had completely dissolved.

The samples were then dispensed through foam actuators. Example 18 foamed a dry, cold foamed structure, while Control O formed a sticky, bubbly liquid. Control O has a somewhat higher ratio of polar to non-polar propellant than Example 10. After propellant loss during discharge (with loss of the polar propellant favored), the solvent action with Control O is still too good for a foamed structure to form.

The foamed structure obtained by expelling 7.1 g of Example 18 had a minimum temperature of $-34°$ C. and required 9 minutes to warm to 0° C., with the ambient temperature at 25° C.

Using the procedure described in Example 10, it was found that the foamed structure from 7.1 g of expelled Example 18 product contained 83% propellant after 60 seconds.

EXAMPLE 19

|  | Parts By Weight | |
| --- | --- | --- |
|  | Example 19 | Control O |
| Isobutyl methacrylate polymer (Elvacite 2045) | 6.8 | 7.6 |
| Triethyl citrate (Citroflex 2) | 1.1 | 1.2 |
| Mineral Oil, 65–75 SSU (Drakeol 7) | 10.5 | |
| Isobutane | 52.6 | 58.8 |
| 1,1-difluoroethane | 29.0 | 32.4 |

All the ingredients except the propellants were placed in an aerosol can. The valve was clinched on, the liquefied propellants were added through the valve, and the can was shaken on a paint shaker until the polymer had completely dissolved.

Example 19 was dispensed through a foam actuator, and formed a cold, oily foamed structure suitable for use as an applicator.

Example 19 contains the same ratio of polar to nonpolar propellant as Control O. However, the presence of the mineral oil changes the solvent balance, so that a small preferential loss of the polar propellant during dispensing, due to evaporation, results in a foamed structure, unlike Control O.

A 5.6 g sample of Example 19 was expelled and the temperature of the resulting foam was measured, as in Example 10. It has a minimum temperature of $-29°$ C.

and required 6 minutes to warm to 0° C., with the ambient temperature at 26° C.

Using the procedure described in Example 10, it was found that the foamed structure from 4.7 g of expelled Example 19 product contained 53% propellant after 60 seconds.

EXAMPLE 20

|  | Parts By Weight Example 20 |
|---|---|
| Ethyl hydroxyethyl cellulose, high viscosity | 5.7 |
| Octyl dodecanol (Standamul G) | 0.8 |
| Corn Oil | 6.9 |
| Imidazoline dicarboxylic coconut derivative sodium salt 10% concentrate in water (Miranol C2M-SF) | 17.1 |
| Isobutane | 38.2 |
| 1,1-difluoroethane | 31.3 |

All the ingredients except the propellants were placed in an aerosol can. The valve was clinched on, and the liquefied propellants added through the valve. The can was then shaken on a paint shaker until the polymer had dissolved.

A portion of the Example 20 composition was dispensed through a foam actuator, and gave a foamed structure that was cold and damp. It could be used as an applicator.

The foamed structure obtained by expelling 7.0 g of sample onto a paper towel had a minimum temperature of −18° C., and required 10 minutes to warm to 0° C., at an ambient temperature of 25° C.

Using the procedure described in Example 10, it was found that the foamed structure from 5.6 g of expelled Example 20 product contained 31% propellant after 60 seconds.

EXAMPLE 21

|  | Parts By Weight | | |
|---|---|---|---|
|  | Example 21 | Control P | Control Q |
| Ethyl hydroxyethyl cellulose, high viscosity | 6.4 | 6.4 | 6.4 |
| Propylene glycol monostearate, pure | 3.4 | 3.4 | 3.4 |
| Octyl dodecanol (Standamul G) | 4.4 | 4.4 | 4.4 |
| Mineral Oil, 340-365 SSU (Drakeol 35) | 16.8 | — | 16.8 |
| Imidazoline monocarboxylic stearyl derivate, sodium salt 10% concentrate in water (Miranol DM-SF) | 5.0 | 5.0 | — |
| Propylene glycol | 1.7 | 1.7 | 1.7 |
| Isobutane | 49.8 | 49.8 | 49.8 |
| Propane | 12.5 | 12.5 | 12.5 |

All the ingredients except the propellants were placed in an aerosol can. The valve was clinched on, and the liquefied propellants were added through the valve. The can was then shaken on a paint shaker until the polymer had completely dissolved.

The product was dispensed through a foam actuator, and produced a cold, oily foam structure, suitable for use as a compress.

Control P and Control Q on the other hand, in which the mineral oil or the aqueous solution had been omitted, gave an ointment, rather than a foamed structure.

The octyl dodecanol functions as a co-solvent. If less had been used, two liquid layers containing propellant would have formed in the can, and these would mix to form a crude emulsion which would be expelled unevenly and with spitting. If more had been used, the product would have formed an ointment.

A 6.2 g sample of Example 21 was expelled onto a paper towel. The foamed structure had a minimum temperature of −13° C. It required 10 minutes for the structure to warm to 0° C., at an ambient temperature of 25° C.

Using the procedure described in Example 10, it was found that the foamed structure from 5.0 g of expelled Example 21 product contained 44% propellant after 60 seconds.

Having regard to the foregoing disclosure, the following is claimed as patentable inventive embodiments thereof:

1. A synthetic polymer-liquefied propellant composition capable of forming a cold foamed structure having a temperature at least 30° C. below the ambient temperature at which the cold foamed structure is formed, and containing open and/or closed cells, which may contain an additive which is deposited in the pores and/or walls of the foamed structure as the foamed structure is formed, comprising, as the essential ingredients:
   (a) a film-forming synthetic polymer in an amount within the range from about 2% to about 30% by weight of the composition;
   (b) at least one liquefied propellant boiling below −10° C.;
   (c) the total propellant being in an amount within the range from about 50% to about 90% by weight of the composition; and having a heat vaporization of at least 55 calories per gram; the propellant being capable of dissolving the synthetic polymer at least in the presence of a co-solvent that is soluble in the propellant and in solutions of the synthetic polymer in the propellant at ambient temperature; and
   (d) at least one nonsolvent that is soluble in the propellant but in which the synthetic polymer is insoluble in an amount within the range from about 1% to about 85% by weight of the composition;
the composition forming on volatilization of propellant at ambient temperature a coherent foamed structure containing open and/or closed cells, and having a temperature at least 30° C. below ambient temperature.

2. A synthetic polymer-propellant composition according to claim 1 in which the propellant is the nonsolvent liquid and including a co-solvent in an amount sufficient to dissolve the synthetic polymer in the co-solvent propellant.

3. A synthetic polymer-propellant composition according to claim 2 in which the propellant is a hydrocarbon propellant.

4. A synthetic polymer-propellant composition according to claim 1 in which there are two propellants, the nonsolvent liquid being the second propellant in which the synthetic polymer is less soluble than in the first propellant.

5. A synthetic polymer-propellant composition according to claim 4 in which the two propellants are a hydrocarbon propellant and dimethyl ether.

6. A synthetic polymer-propellant composition according to claim 4 in which the two propellants are a hydrocarbon propellant and 1,1-difluoroethane.

7. A synthetic polymer-propellant composition according to claim 1 in which the nonsolvent in which the synthetic polymer is insoluble is present in sufficient amount to form at least two liquid phases, each phase containing synthetic polymer and propellant, and at least one phase containing nonsolvent liquid.

8. A synthetic polymer-propellant composition according to claim 7 in which the synthetic polymer is selected from the group consisting of cellulose derivatives and polymethacrylates.

9. A synthetic polymer-propellant composition according to claim 7 in which the nonsolvent liquid is selected from the group consisting of mineral oil, vegetable oil, and silicone oil.

10. A synthetic polymer-propellant composition according to claim 1 in which the propellant comprises at least one polar propellant that is water-soluble in an amount of at least 0.2% by weight at 21° C., and the nonsolvent is selected from the group consisting of:
 (i) a nonpolar liquefied propellant with a lower vapor pressure than the polar liquefied propellant;
 (ii) a liquid or solid nonsolvent that is not a solvent for the polymer but is soluble in the propellant;
 (iii) water; and
 (iv) aqueous solutions.

11. A synthetic polymer-propellant composition according to claim 10 in which the polymer is a cellulose derivative.

12. A synthetic polymer-propellant composition according to claim 10 in which the polymer is polymethacrylate.

13. A synthetic polymer-propellant composition according to claim 10 in which the polar propellant is dimethyl ether.

14. A synthetic polymer-propellant composition according to claim 10 in which the polar propellant is 1,1-difluoroethane.

15. A synthetic polymer-propellant composition according to claim 10 in which the nonpolar liquefied propellant with a lower vapor pressure than the polar liquefied propellant is a hydrocarbon propellant.

16. A synthetic polymer-propellant composition according to claim 10 in which the nonsolvent is selected from the group consisting of mineral oil, vegetable oil and silicone oil.

17. A synthetic polymer-propellant composition according to claim 10 in which the nonsolvent is water or an aqueous solution.

18. A synthetic polymer-propellant composition according to claim 1 in which the synthetic polymer is a cellulose derivative and the composition contains both nonsolvent for the polymer and water or an aqueous solution.

* * * * *